US009999350B2

(12) United States Patent
Heeren

(10) Patent No.: US 9,999,350 B2
(45) Date of Patent: Jun. 19, 2018

(54) REDUCED GLARE SURGICAL MICROSCOPE AND ASSOCIATED DEVICES, SYSTEMS, AND METHODS

(71) Applicant: Novartis AG, Basel (CH)

(72) Inventor: Tammo Heeren, Aliso Viejo, CA (US)

(73) Assignee: Novartis AG, Basel (CH)

(*) Notice: Subject to any disclaimer, the term of this patent is extended or adjusted under 35 U.S.C. 154(b) by 329 days.

(21) Appl. No.: 14/496,446

(22) Filed: Sep. 25, 2014

(65) Prior Publication Data

US 2016/0089026 A1 Mar. 31, 2016

(51) Int. Cl.
A61B 3/14 (2006.01)
A61B 3/10 (2006.01)
A61B 3/02 (2006.01)
A61B 3/00 (2006.01)
A61B 3/15 (2006.01)
A61B 3/13 (2006.01)
(Continued)

(52) U.S. Cl.
CPC ............ *A61B 3/156* (2013.01); *A61B 3/0025* (2013.01); *A61B 3/13* (2013.01); *G02B 21/0012* (2013.01); *G02B 27/0018* (2013.01); *G02F 1/1313* (2013.01); *G02F 1/13318* (2013.01)

(58) Field of Classification Search
CPC ........... A61B 3/103; A61B 3/113; A61B 3/14; A61B 3/125; A61B 3/1225; A61B 3/024; A61B 3/1015; A61B 3/107; G02B 27/0103; G02B 27/0172; G02B 27/0149
USPC ................. 351/209, 200, 205–206, 210, 219, 351/221–222, 246–247; 359/13, 630–633
See application file for complete search history.

(56) References Cited

U.S. PATENT DOCUMENTS 3,822,926 A 7/1974 Dalbera et al.
5,121,251 A 6/1992 Edwards
(Continued)

FOREIGN PATENT DOCUMENTS

GB 680221 A 10/1952
GB 1436037 A 5/1976
(Continued)

OTHER PUBLICATIONS

International Searching Authority, International Search Report, PCT/US2015/050182, dated Nov. 16, 2015, 5 pages.
(Continued)

*Primary Examiner* — Dawayne A Pinkney

(57) ABSTRACT

Devices, systems, and methods for glare reduction in surgical microscopy are provided. A method of operating a surgical microscope may include: receiving light reflected from the surgical field at an image sensor; processing the received light to generate image data; identifying portions of the image data representative of glare; and controlling an optical element to limit the transmission of light associated with the glare. A surgical microscope may include: an image sensor configured to receive light reflected from the surgical field, a computing device, and an optical element. The computing device may be configured to: identify portions of the light received at the image sensor associated with glare and generate a control signal to limit the transmission of the light associated with the glare. The optical element may be configured to selectively limit the transmission of the light associated with the glare in response to the control signal.

20 Claims, 6 Drawing Sheets

(51) Int. Cl.
*G02B 21/00* (2006.01)
*G02F 1/13* (2006.01)
*G02F 1/133* (2006.01)
*G02B 27/00* (2006.01)

(56) References Cited

U.S. PATENT DOCUMENTS

| | | |
|---|---|---|
| 5,351,151 A | 9/1994 | Levy |
| 5,687,251 A | 11/1997 | Erler et al. |
| 6,373,626 B1 | 4/2002 | Tanaka et al. |
| 7,023,613 B2 | 4/2006 | Kitajima |
| 7,234,824 B2 | 6/2007 | Langley |
| 7,282,723 B2 | 10/2007 | Schomacker et al. |
| 7,452,067 B2 * | 11/2008 | Gross ............... 351/45 |
| 8,033,672 B2 | 10/2011 | Richter |
| 2006/0215076 A1 | 9/2006 | Karim |
| 2008/0269883 A1 | 10/2008 | Das et al. |
| 2010/0039700 A1 | 2/2010 | Ghosh et al. |
| 2010/0149483 A1 | 6/2010 | Chiavetta, III |
| 2011/0160578 A1 | 6/2011 | Tripathi et al. |
| 2013/0242262 A1 | 9/2013 | Lewis |
| 2014/0063377 A1 * | 3/2014 | Castelberg et al. ......... 349/14 |
| 2015/0173644 A1 | 6/2015 | Ren et al. |

FOREIGN PATENT DOCUMENTS

| | | |
|---|---|---|
| JP | 03571112 B2 | 9/2004 |
| WO | 97/16762 A1 | 5/1997 |
| WO | 03/034123 A1 | 4/2003 |
| WO | 2007/053591 A2 | 5/2007 |
| WO | 2013/071153 A1 | 5/2013 |

OTHER PUBLICATIONS

International Searching Authority, Written Opinion of the International Searching Authority, PCT/US2015/050182, dated Nov. 16, 2015, 5 pages.

Website archive of http://www.imagemagick.org dated Sep. 6, 2013; accessed from https://web.archive.org/web/20130906202627/http://www.imagemagick.org/script/index.php on Dec. 7, 2015 (3 pages).

* cited by examiner

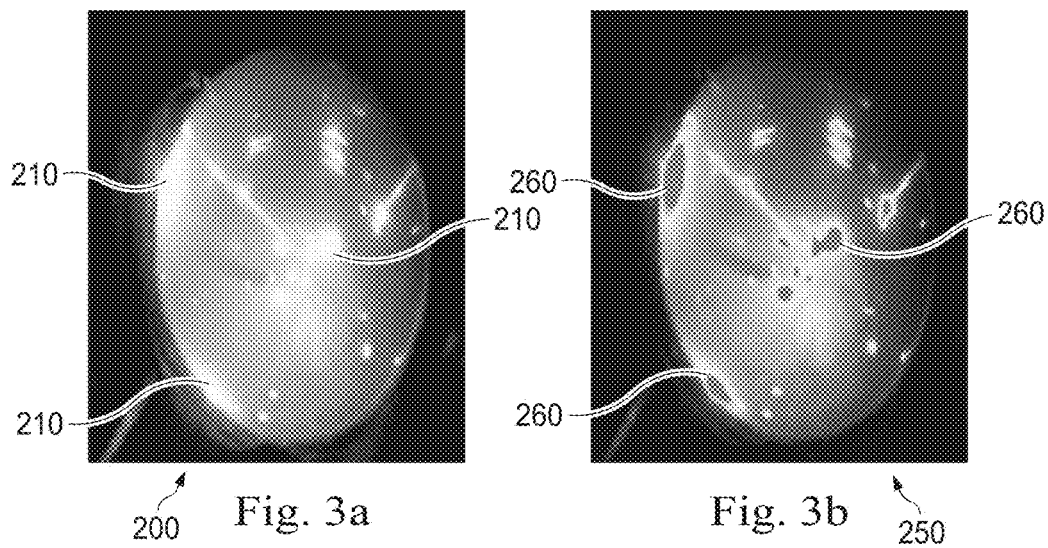
Fig. 3a  Fig. 3b
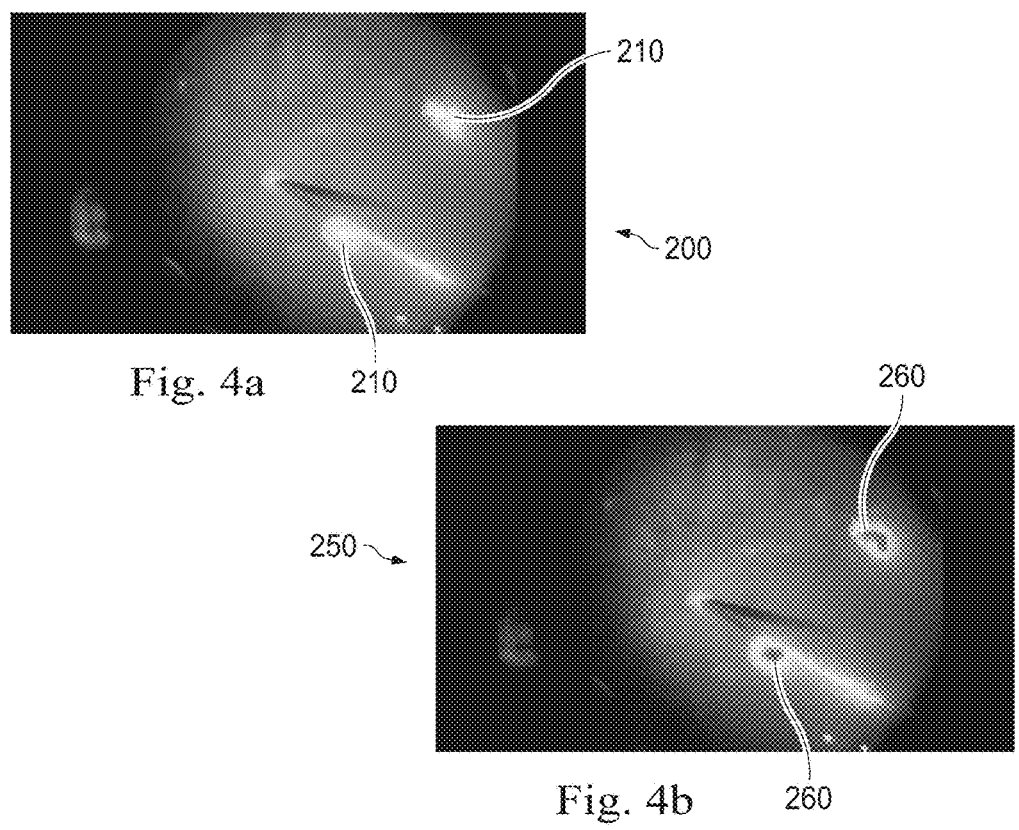
Fig. 4a
Fig. 4b

REDUCED GLARE SURGICAL MICROSCOPE AND ASSOCIATED DEVICES, SYSTEMS, AND METHODS

TECHNICAL FIELD

Embodiments disclosed herein are related to surgical microscopes. More specifically, embodiments described herein relate to microscopes including an optical element controllable to selectively reduce glare from light reflected from a surgical field.

RELATED ART

Doctors can use surgical microscopes during surgical procedures to see fine details of a patient's anatomy (e.g., details of a patient's eye during ophthalmic surgical procedure). A successful procedure can depend on the doctor's ability to view the patient's anatomy clearly using the microscope. One impediment to a doctor's ability to view the patient's anatomy through the surgical microscope is glare from the surgical field.

In some instances of ophthalmic surgery, glare occurs as a result of a fluid-air interface in a patient's eye. For example, a vitreoretinal surgery involving treatment of retinal detachment or a macular hole can include a fluid-air exchange. During the fluid-air exchange, saline solution introduced into the eye during the surgical procedure is aspirated through, e.g., a vitreoretinal cutter or extrusion cannula, and replaced with air. The air can serve as a tamponade agent to hold the retina in position and/or close the macular hole after the surgical intervention. Bright, background intraocular illumination can be provided by, e.g., a chandelier during the surgery. This illumination persists during the fluid-air exchange to provide the surgeon continuing vision of the patient's eye. During the fluid-air exchange, the eye is partially filled with fluid that is yet to be aspirated (e.g., at the bottom of eye) and partially filled with air in the space previously occupied by the fluid (e.g., at the top of the eye). Between the air and the fluid is a fluid-air interface. As the fluid-air exchange progresses, the fluid previously surrounding the light source can be aspirated such that the light source becomes surrounded by air. The light source transmits bright light towards the fluid-air interface. The interface reflects this light or glare towards the surgeon, who is viewing the patient's eye through the surgical microscope. As shown in FIGS. 3a, 4a, and 5a, glare spots 210 are visible in images 200 of the surgical field viewed through a conventional surgical microscope.

The glare from the fluid-air interface is problematic for several reasons. For example, the glare can saturate the surgeon's visual field and make it difficult for the surgeon to see the patient's eye. As another example, the glare can also persist in the surgeon's visual field even when the surgeon blinks or looks away from the surgical microscope. This can be disruptive to the surgical procedure because it takes extra time for the lingering effects from the glare to pass and for the surgeon to see clearly again.

Some efforts have been made to reduce sources of reflection in the surgical field. For example, surgical instruments have been made less reflective using surface treatments to the make the exterior rougher. Light sources have also been designed so as not the shine directly towards the surgeon. However, the glare caused by the light source directing light at the fluid-air interface remains. The illumination from the light cannot be stopped because the surgeon needs to have continuing vision of the surgical field, and there is little other light shining into the eye during the fluid-air exchange. The fluid-air interface itself cannot be eliminated during surgical procedures in which the fluid-air exchange has therapeutic benefits.

The devices, systems, and methods disclosed herein address one or more of the deficiencies of the prior art.

SUMMARY

The presented solution fills an unmet medical need with a unique solution to provide a surgical microscope with an optical element that is controllable to selectively limit the transmission of light associated with glare from a surgical field to an observer. While several examples are provided herein for an ophthalmic surgical microscope, it is to be understood that the devices, systems, and methods described herein could also be applied to microscopes for other types of surgical procedures requiring a surgical microscope.

Consistent with some embodiments, a method of operating an ophthalmic surgical microscope positioned in an optical pathway between a surgical field and an observer includes: receiving light reflected from the surgical field at an image sensor of the ophthalmic surgical microscope; processing the received light to generate image data; identifying portions of the image data representative of glare from the surgical field; and controlling an optical element positioned in the optical pathway to limit the transmission of light associated with the glare.

In some embodiments, the method further includes identifying portions of the optical element through which the light associated with the glare will be transmitted to the observer that correspond with the identified portions of the image data. In some embodiments, controlling an optical element includes generating a control signal that selectively controls the identified portions of the optical element to limit the transmission of the light associated with the glare. In some embodiments, controlling an optical element includes controlling portions of the optical element other than the identified portions to transmit the light reflected from the surgical field to the observer. In some embodiments, the method further includes receiving, at a user interface of the ophthalmic surgical microscope, a user-specified dimming parameter to limit the transmission of light through the identified portions of the optical element. In some embodiments, identifying portions of the image data includes identifying portions of the image data having a brightness value greater than a threshold brightness parameter. In some embodiments, the method further includes receiving, at a user interface of the ophthalmic surgical microscope, a user-specified threshold brightness parameter. In some embodiments, the method further includes modifying the identified portions of the image data to limit the glare in a visual representation of the image data. In some embodiments, the method further includes providing the visual representation to a display device. In some embodiments, the optical element comprises a liquid crystal array. In some embodiments, controlling an optical element includes providing the control signal to a voltage source in communication with the liquid crystal array. In some embodiments, the method further includes providing a voltage to the liquid crystal array based on the control signal such that pixels of the liquid crystal array through which the light associated with the glare will be transmitted to the observer are modified to limit the transmission of the light. In some embodiments, controlling an optical element includes limiting the transmission of light associated with the glare while not limiting the transmission of light that is not associated with the glare. In some embodiments, controlling an optical element includes limiting the transmission of light associated with the glare in a manner different than the transmission of light not associated with the glare. In some embodiments, the optical element is disposed in a module removably coupled to the ophthalmic surgical microscope. In some embodiments, the optical element and the image sensor are disposed in a module removably coupled to the ophthalmic surgical microscope.

Consistent with some embodiments, an ophthalmic surgical microscope positioned in an optical pathway between an observer and a surgical field can include: an image sensor configured to receive light reflected from the surgical field; a computing device in communication with the image sensor, the computing device configured to: identify portions of the light received at the image sensor associated with glare from the surgical field; and generate a control signal to limit the transmission of the light associated with the glare to the observer; and an optical element in communication with the computing device and configured to selectively limit the transmission of the light associated with the glare to the observer in response to the control signal.

In some embodiments, the computing device is further configured to identify, based on the identified portions of the light received at the image sensor, corresponding portions of the optical element through which the light associated with the glare will be transmitted to the observer. In some embodiments, the optical element is controllable to selectively limit the transmission of the light associated with the glare through the identified portions of the optical element. In some embodiments, ophthalmic surgical microscope further includes a user interface configured to receive a user-specified dimming parameter to limit the transmission of light through the identified portions of the optical element, the computing device configured generate the control signal to limit the transmission of the light associated with the glare based on the user-specified dimming parameter. In some embodiments, the computing device is configured to identify portions of the light received at the image sensor associated with glare from the surgical field by identifying portions of the light received at the image sensor having a brightness value greater than a threshold brightness parameter. In some embodiments, the ophthalmic surgical microscope further includes a user interface configured to receive a user-specified threshold brightness parameter, the computing device configured to generate the control signal to limit the transmission of the light associated with the glare based on the user-specified threshold brightness parameter. In some embodiments, the optical element comprises a liquid crystal array. In some embodiments, the ophthalmic surgical microscope further includes a voltage source in communication with the optical element, the computing device configured to provide the control signal to the voltage source. In some embodiments, the voltage source is configured to provide a voltage to the liquid crystal array based on the control signal such that pixels of the liquid crystal array through which the light associated with the glare will be transmitted to the observer are modified to limit the transmission of the light. In some embodiments, the optical element and the voltage source are disposed in a removable module. In some embodiments, the optical element, the voltage source, and the image sensor are disposed in a removable module. In some embodiments, the optical element, the voltage source, the image sensor, and the computing device are disposed in a removable module. In some embodiments, the optical element is disposed in a removable module.

Consistent with some embodiments, an ophthalmic surgical microscope positioned in an optical pathway between an observer and a surgical field can include: an image sensor configured to receive light reflected from the surgical field; a computing device in communication with the image sensor, the computing device configured to: identify portions of the light received at the image sensor having a brightness value exceeding a threshold brightness parameter; and generate a control signal to limit the transmission of the light having a brightness value exceeding a threshold brightness parameter; and an optical element in communication with the computing device and configured to selectively limit the transmission of the light having a brightness value exceeding a threshold brightness parameter, wherein the computing device is further configured to identify portions of the optical element through which light having a brightness value exceeding a threshold brightness parameter will be transmitted and to generate the control signal to selectively limit the transmission of light through the identified portions of the optical element.

In some embodiments, the optical element is disposed in a removable module. In some embodiments, the optical element and the image sensor are disposed in a removable module. In some embodiments, the optical element, the image sensor, and the computing device are disposed in a removable module.

Additional aspects, features, and advantages of the present disclosure will become apparent from the following detailed description.

BRIEF DESCRIPTION OF THE DRAWINGS

FIG. 3a is an image of a surgical field viewed through a conventional ophthalmic surgical microscope.

FIG. 3b is a simulated image of the surgical field of FIG. 3a that may be viewed through an ophthalmic surgical microscope according to an aspect of this disclosure.

FIG. 4a is an image of a surgical field viewed through a conventional ophthalmic surgical microscope.

FIG. 4b is a simulated image of the surgical field of FIG. 4a that may be viewed through an ophthalmic surgical microscope according to an aspect of this disclosure.

Figure 1:
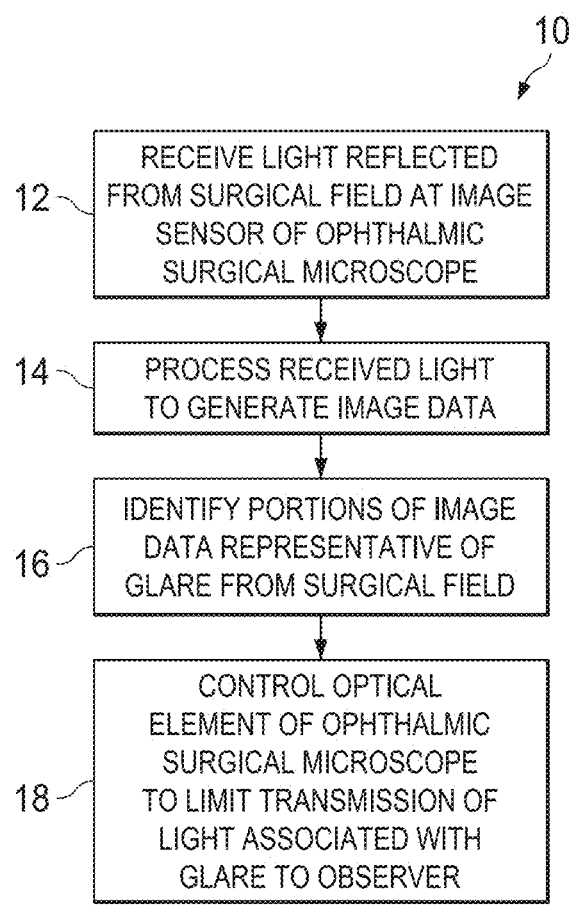
FIG. 1 is a flow diagram of a method of operating an ophthalmic surgical microscope positioned in an optical pathway between a surgical field and an observer.

In the drawings, elements having the same designation have the same or similar functions.

DETAILED DESCRIPTION

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

The present disclosure describes an ophthalmic surgical microscope with an image sensor/camera and a controllable optical element. Light reflected from the surgical field can be received at the image sensor/camera. A computing device in communication with the image sensor/camera can determine portions of the light associated with glare from the surgical field. The computing device can generate a control signal to cause the optical element to selectively limit the transmission of light associated with the glare. Thus, the optical element provides real time visual correction for the glare. In some embodiments, the optical element is a liquid crystal array. A voltage can be applied to the liquid crystal array in response to the control signal. Pixels, of the liquid crystal array, representing the light associated with the glare can be controlled to limit the transmission of the light.

The devices, systems, and methods of the present disclosure provide numerous advantages, including: (1) improving efficacy of surgical procedures by providing greater spatial awareness for the doctor; (2) improving microscope optics by limiting disruptive, high brightness light; and (3) increasing usability for surgical microscopes by maximizing surgical field sight for all doctors.

FIG. 1 provides a flow diagram of a method 10 of operating an ophthalmic surgical microscope. The method 10 can be further understood with reference to FIGS. 2-5b. The method 10 can be implemented during an ophthalmic surgical procedure in which a fluid-air exchange is conducted or any other surgical procedure in which high brightness light is reflected from the surgical field. At 12, light reflected from a surgical field may be received at an image sensor of an ophthalmic surgical microscope.

Figure 2A:
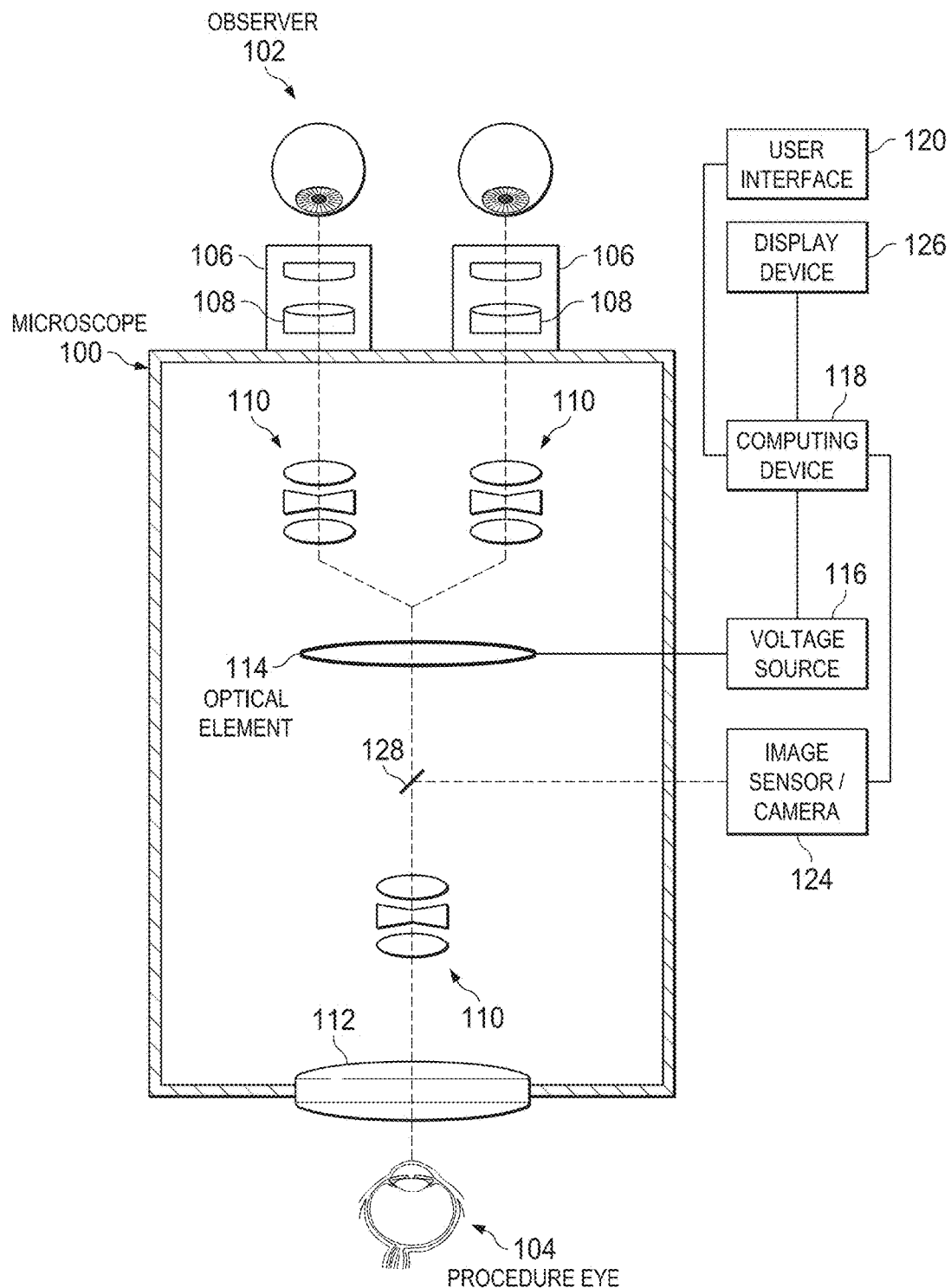
FIG. 2a is a diagram illustrating an exemplary ophthalmic surgical microscope according to an aspect of this disclosure.

FIG. 2a illustrates an exemplary ophthalmic surgical microscope 100. The microscope 100 can be disposed in an optical pathway between an observer 102 and a surgical field. The observer 102 can view the surgical field, such as a procedure eye 104, using the microscope 100. Depending on the particular application, the observer 102 can be a healthcare professional, such as a doctor or surgeon performing, monitoring, and/or observing a diagnostic, surgical, and/or other medical procedure. The procedure eye 104 represents a surgical site and can be that of a patient undergoing the medical procedure.

The optical train of the microscope 100 may include one or more lenses, mirrors, filters, gratings, and/or other optical components. The optical components can be positioned in the optical pathway of light reflected from the surgical field. For example, eyepieces 106 can include optical components 108, and the body of the microscope 100 can include optical components 110 and objective lens 112. The optical components 108 and 110, and objective lens 112 are exemplary, and in various embodiments, the microscope 100 can include more or fewer lenses and/or other optical components to focus the light and/or magnify the image.

The image sensor/camera 124 can be positioned in the optical pathway of the light reflected from the surgical field. In this embodiment, the microscope 100 includes one or more beam splitters 128 to direct at least a portion of the light to the imaging sensor/camera 124. Depending on the embodiment, the image sensor/camera 124 can include a charge-coupled device (CCD) sensor, a complementary metal-oxide-semiconductor (CMOS) sensor, or other suitable image sensor. The image sensor/camera 124 is configured to receive and capture light reflected from the surgical field. In some embodiments, the image sensor/camera 124 is part of the microscope 100. In some embodiments, the image sensor/camera 124 is a separate component that is not part of the microscope 100 itself and is rather in communication with, e.g., a computing device 118 and the microscope 100.

Referring again to FIG. 1, at 14, the received light may be processed to generate image data. In some embodiments, the image sensor/camera 124 can include circuitry to generate electrical signal(s) and/or image data representative of the received light. The image sensor/camera 124 can be in communication with a computing device 118 (FIG. 2). The image sensor/camera 124 can provide the image data to the computing device 118. In some embodiments, the computing device 118 generates the image data when electrical signal(s) representative of the received light are received from the image sensor/camera 124. Processing the received light can include any one or more signal processing steps. The computing device 118 can include any suitable processor, memory, or processing circuit for processing the light received at the image sensor/camera 124, electrical signal(s), and/or image data, and other steps described herein or necessary to accomplish the steps described herein. In some embodiments, the computing device 118 is part of the microscope 100. In some embodiments, the computing device 118 is a separate component that is not part of the microscope 100 itself and is rather in wired or wireless communication with, e.g., the voltage source 116 and the microscope 100.

Referring again to FIG. 1, at 16, the method 10 can include identifying portions of the image data or the light received at the image sensor representative of glare from the surgical field. For example, the glare spots 210 in the images 200 (FIGS. 3a, 4a, and 5a) can be identified. The images 200 are representative of an observer's view through a conventional surgical microscope, while the images 250 (FIGS. 3b, 4b, and 5b) are representative of images through the exemplary devices described herein. The images 200 can also be understood as visual representations of the light received at the image sensor/camera 124 of the microscope 100. Glare from the surgical field can be characterized by such a high brightness as to be disruptive to the surgical procedure. Thus, at 16, portions of the image data or the light received at the image sensor, having a brightness value greater than a threshold brightness parameter, may also be identified. The brightness value can be any numerical description of luminance. For example, the brightness value can be representative of the amount of light that passes through or is received at a particular area (e.g., of the image sensor/camera 124, of the optical element 114, etc.). For example, light received at each pixel of the image sensor/camera 124 can have an associated brightness value. In some examples, each portion or subdivision of the images 200 can be characterized by the brightness value. In some embodiments, the brightness value can be a percentage, e.g., at a particular pixel of the image sensor/camera 124, of the total brightness of light reflected from the surgical field.

The threshold brightness parameter is selected, in some exemplary embodiments, to correspond with a maximum amount of light that can be present in the surgical field without disrupting the surgeon's vision. In some embodiments, the threshold brightness parameter is a brightness level that is fixed when the microscope 100 is manufactured. In some embodiments, the threshold brightness parameter can be a variable quantity that is adjustable during the surgical procedure or during surgical preparation. In some embodiments, the observer 102 can adjust the threshold brightness parameter based on his or her tolerance for bright light, illumination preferences, etc. In some embodiments, the computing device 118 utilizes the threshold brightness parameter to determine which portions of light reflected from the surgical field are classified as glare. For example, the observer 102 may select a lower threshold parameter to decrease the brightness level viewed through the microscope 100. This in turn may cause the computing device 118 to identify a relatively larger percentage of light as representative of glare at 16 (and limited by the optical element 114, as described below). Likewise, the observer 102 may select a higher threshold parameter to increase the brightness level viewed through the microscope 100. As a result, the computing device 118 identifies a relatively smaller percentage of light as representative of glare at 16 (and limited by the optical element 114). For example, a user specified threshold brightness parameter can be received at a user interface 120 (FIG. 2). The user interface 120 can be in communication with the computing device 118 such that, e.g., the user specified threshold brightness parameter is transmitted by the user interface 120 and received at the computing device 118. In some embodiments, the brightness value and/or the threshold brightness parameters can be described by electrical signal(s) representative of the light received at the image sensor/camera 124. In such embodiments, light associated with the glare can be identified using one or more electronic components to filter signals associated with high brightness light.

Figure 5A:
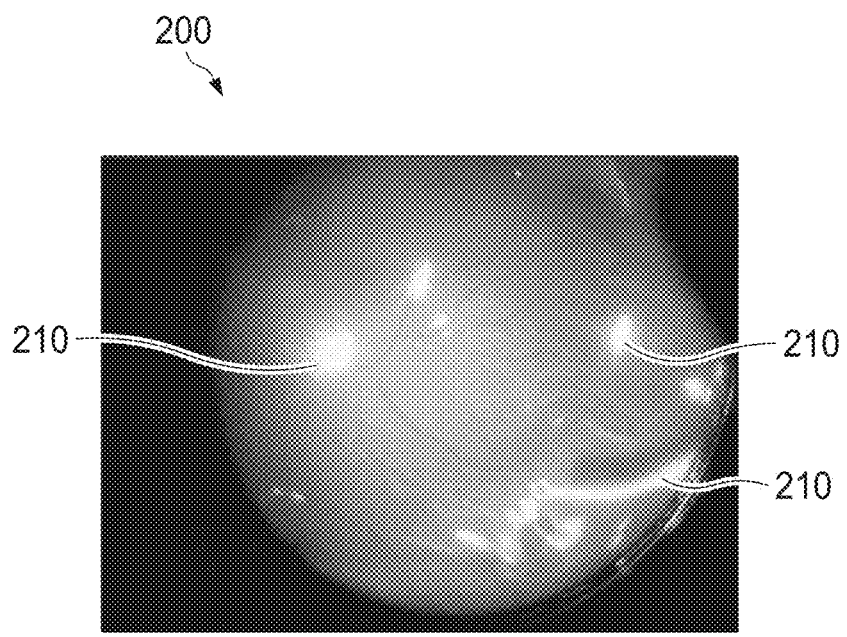
FIG. 5a is an image of a surgical field viewed through a conventional ophthalmic surgical microscope.

Some portions of the images 200 in FIGS. 3a, 4a, and 5a are brighter than other portions. This can occur in the ordinary course of a surgical procedure. Thus, the brightness value for some portions of the images 200 is higher (e.g., indicative of more luminance) than for other portions. Some localized instances of brightness in the visual field can be tolerable to the observer 102, while other instances can be disruptive to the surgical procedure. The threshold brightness parameter can be selected or set such that the computing device 118 identifies portions of the images 200 with disruptively high brightness at 16. When the brightness value exceeds the threshold brightness parameter at a given portion of the image 200, the computing device 118 identifies a glare spot 210. Note that, for clarity, only some glare spots 210 are labeled in FIGS. 3a, 4a, and 5a.

The user interface 120 can be in communication with the computing device 118. The user interface 120 is a component of the computing device 118 configured to receive input(s) from an observer 102. In some embodiments, the user interface 120 is part of the microscope 100. In some embodiments, the user interface 120 is a separate component that is not part of the microscope 100 itself and is rather in communication with the computing device 118 and the microscope 100. The user interface 120 can include input devices or systems, including by way of non-limiting example, a keyboard, a mouse, a joystick, a touchscreen, dials, and buttons, among other input devices. The user interface 120 can be a display (including, for example, a touchscreen display) configured to present images or other data (e.g., microscope settings, display settings, etc.) to a user, such as images of surgical field during the surgical procedure.

Referring again to FIG. 1, at 18, the method 10 can include controlling an optical element to limit the transmission of the light associated with the glare to the observer. As shown in FIG. 2, the microscope 110 includes the optical element 114. In some exemplary embodiments describe herein, portions or subdivisions of the optical element 114 can be individually and selectively controlled to limit the transmission of light using the control signal. Thus, various portions of the optical element 114 can permit different amounts of light to pass through to the observer 102. In some embodiments, the optical element 114 is a liquid crystal array. In examples where the optical element 114 is a liquid crystal array, the computing device 118 may be configured to selectively control, directly or indirectly, the individual pixels of the liquid crystal array to limit the transmission of light. The liquid crystal array can include one or more layers or components, including polarizing filter(s), glass substrate(s), liquid crystal layer(s), etc. The computing device 118 can be configured to generate the control signal to limit the transmission of light. The optical element 114 can be configured to selectively limit the transmission of light associated with the glare to the observer 102 in response to the control signal. At 18, a mask may be applied at localized areas of brightness in the visual field of the observer 102, as opposed to applying the mask across the entire visual field. In some embodiments, the optical element 114 can be controlled to apply a mask across the entire visual field.

The optical element 114 can be positioned in the optical pathway between the observer and the surgical field. In different embodiments, the optical element 114 can be positioned at various locations in the optical train of the microscope 100. For example, depending on the embodiment, the optical element 114 can be positioned between the optical components 108 and the optical components 110, between the optical components 110 and the objective lens 112, between the observer 102 and the objective lens 112, between the observer 102 and the beam splitter 128, or at other locations. Some microscope 100 embodiments include more than one optical element 114. The number of optical elements 114 may depend on, among other factors, where in the optical pathway and/or the optical train of the microscope 100 the optical elements 114 are positioned. For example, FIG. 2 shows one movable optical element 114 positioned between the observer 102 and the beam splitter 128 that guides at least a portion of the light reflected from the surgical field to the image sensor/camera 124. The optical element 114 can be positioned in the optical pathway past the beam splitter 128 such that the image sensor/camera 124 receives unfiltered light from the surgical field. The image sensor/camera 124 and/or the computing device 118 can use the unfiltered light to identify portions thereof associated with glare. The computing device 118 can generate a control signal that controls the optical element 114 in a manner causing the optical element 114 to limit the transmission of the light associated with the glare. Some embodiments include more than one optical element 114 positioned in separate optical pathways respectively associated with each eye of the observer 102 (e.g., in a stereo microscope).

Figure 5B:
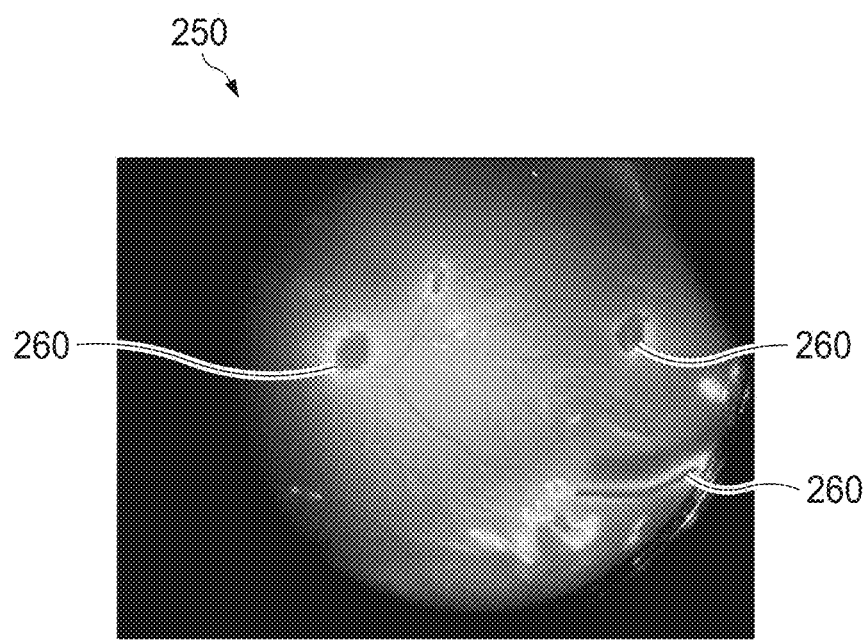
FIG. 5b is a simulated image of the surgical field of FIG. 5a that may be viewed through an ophthalmic surgical microscope according to an aspect of this disclosure.

FIGS. 3b, 4b, and 5b show simulated images 250 of the surgical field viewed through the surgical microscope 100. Simulated images 250 include dimmed spots 260 where glare spots 210 occurred in the images 200 (FIGS. 3a, 4a, and 5a). Dimmed spots 260 occur as a result of the light associated with the glare being completely and/or partially blocked by the optical element 114. Light associated with other portions of the images 250 (e.g., other than those associated with the glare) are permitted to pass through the optical element 114 without being blocked.

In some embodiments, the method 10 includes, identifying, based on the identified portions of the image data representative of the glare from the surgical field (at 16), corresponding portions of the optical element 114 through which the light associated with the glare will be transmitted to the observer. For example, the computing device 118 can associate one or more pixels of the image sensor/camera 124 at which the light is received and one or more pixels of the optical element 114 through which the light will be transmitted. For example, a one-to-one correspondence can be determined between location(s) of incident light on the image sensor/camera 124 and location(s) of incident light on the optical element 114.

The computing device 118 can selectively control, directly or indirectly, individual portions of the optical element 114 (e.g., pixels of the liquid crystal array) to permit all, a portion, or none of the incident light to pass through to the observer 102. In some embodiments, controlling the optical element 114 (at 18) can include selectively controlling the previously identified portions of the optical element through which the light associated with the glare will be transmitted to limit the transmission of the light. In some embodiments, controlling the optical element 114 (at 18) can include generating a control signal that selectively controls the identified portions of the optical element to limit the transmission of the light associated with the glare. The computing device 118 is configured to generate the control signal. For example, the control signal generated by the computing device 118 can cause the previously identified portions of the optical element 114 to partially or completely block the transmission of incident light. At the same time, for example, other portions of the optical element 114 can be controlled to permit all or a different proportion of incident light to pass through. In some embodiments, controlling an optical element (at 18) includes limiting the transmission of light associated with the glare while not limiting the transmission of light that is not associated with the glare. Thus, in some embodiments, controlling the optical element 114 (at 18) can include controlling portions of the optical element, other than the previously identified portions, to transmit light reflected from the surgical field to the observer.

In some embodiments, the computing device 118 provides the control signal directly to the optical element 114. In some embodiments, the control signal is indirectly provided to the optical element 114. For example, in embodiments in which the optical element 114 is a liquid crystal array, controlling the optical element 114 (at 18) can include providing the control signal to a voltage source 116, which, as shown in FIG. 2, is in communication with the optical element 114. Therefore, the method 10 encompasses providing a voltage to the liquid crystal array from the voltage source 116 based on the control signal received from the computing device 118. In some embodiments, the voltage source 116 is part of the microscope 100. In some embodiments, the voltage source 116 is a separate component that is not part of the microscope 100 itself and is rather in communication with the optical element 114, the computing device 118, and/or the microscope 100. The applied voltage can modify the pixels of the liquid crystal array transmitting the light associated with the glare to limit the transmission of the light. For example, the orientation of the liquid crystals can be changed based on the applied voltage to permit transmission of only a desired amount of light. The applied voltage can selectively control individual pixels of the liquid crystal array to allow different amounts of light to pass through. In some embodiments, controlling the optical element 114 (at 18) includes limiting the transmission of light associated with the glare in a manner different than the transmission of light not associated with the glare. For example, at the same time, one subset of pixels can transmit no incident light, a different subset of pixels can transmit some proportion of incident light, yet another subset of pixels can transmit a different proportion of incident light, and still another subset of pixels can transmit all incident light. The liquid crystal array and the voltage source are non-limiting examples. Any other suitable optical element can be implemented in the microscope 100. The voltage source can be described more generally as an actuator. Any other suitable actuator in communication with the optical element and configured to selectively control the transmission of light through individual portions of the optical element can be implemented in the microscope 100.

A dimming parameter can describe how the optical element 114 limits the transmission of incident light. In some embodiments, the computing device 118 utilizes the dimming parameter to determine how much of the light previously identified as glare (at 16) is blocked. For example, the parameter can be representative of a percentage of incident light that that is permitted to pass through one or more portions of the optical element 114. The dimming parameter can represent a percentage of permissible transmission of incident light between approximately 0% and approximately 100% transmission, in increments of 0.5%, 1%, 2%, 5%, 10%, 20%, 25%, 33%, 50%, and other suitable increments. When a higher percentage of incident light is permitted to pass through the optical element 114, the optical element 114 transmits more glare or high brightness light to the observer 102. When a lower percentage of incident light is permitted pass through the optical element 114, the optical element 114 transmits less glare or high brightness light to the observer 102. In some embodiments, the dimming parameter can be fixed when the microscope 100 is manufactured. In some embodiments, the dimming parameter is a variable quantity that is adjustable during the surgical procedure or during surgical preparation. In some embodiments, the observer 102 can adjust the dimming parameter based on his or her tolerance for bright light, illumination preferences, etc. For example, a user specified dimming parameter can be received at the user interface 120. The computing device 118 can generate the control signal based on the user specified dimming parameter such that the optical element 114 limits the transmission of incident light by the desired amount. The control signal can control the optical element 114 such that different portions limit the transmission of incident light by a different amount. The computing device 118 can control, directly or indirectly, a portion of the optical element 114, e.g., through which a relatively greater amount of high brightness light passes to limit a relatively greater amount of the light. At the same time, the computing device 118 can control, directly or indirectly, a different portion of the optical element 114, e.g., through which a relatively lesser amount of high brightness light passes to limit a relatively lesser amount of the light.

The dimming parameter can be selected such that the glare spots 210 (FIGS. 3a, 4a, and 5a) are darkened to be less disruptive to the observer 102 during the surgical procedure. The extent to which light is permitted to pass through various portions of the optical element 114 is illustrated in FIGS. 3b, 4b, and 5b. For example, some portions of the dimmed spots 260 are relatively darker or blacker, indicative of the fact that little or no light is permitted pass through those portions of the optical element 114. The darker or blacker portions can be representative of a dimming parameter associated with transmitting relatively less light. Some portions of the dimmed spots 260 are relatively lighter or greyer, indicative of the fact that little light, but more than the dark or black spots, is permitted to pass through those portions of the optical element 114. The lighter or greyer portions can be representative of a dimming parameter associated transmitting relatively more light.

The dimmed spots 260 can be additionally described by a blurring parameter. The computing device 118 can utilize the blurring parameter to control the smoothness of the visual transition between portions of the optical element 114 that block light and portions of the optical element 114 that permit some or all light to pass through. Controlling the optical element 114 based on the blurring parameter can be described as providing anti-aliasing or edge blur for the dimmed spots 260. For example, as shown in FIGS. 3b, 4b, and 5b, the darker or blacker portions are generally towards the center of the dimmed spots 260, while the lighter or greyer spots are generally towards the periphery of the dimmed spots 260. The computing device 118 can control the optical element 114 to block light in varying degrees. The relatively lowest percentage of light can be blocked at the farthest points from the center of the dimmed spots 260. The percentage of light blocked by the optical element 114 can increase closer to the center of the dimmed spots 260. This can provide smoother edges to the dimmed spots 260. The blurring parameter can describe an area covered by the smoothed edges of the dimmed spots 260. The dimmed spots 260 can be described as Gaussian in that the highest percentage of light is blocked at the center and progressively decreasing percentages are blocked towards the periphery.

In some embodiments, the blurring parameter can be a quantity that is fixed or set when the microscope 100 is manufactured. In some embodiments, the blurring parameter can be a variable quantity that is adjustable during the surgical procedure or during surgical preparation. In some embodiments, the observer 102 can adjust the blurring parameter based on his or her tolerance for bright light, illumination preferences, etc. The computing device 118 can generate a smoother transition between glare spots and non-glare spots by selecting a higher blurring parameter. A smoother transition can be visually less distracting for the observer 102 when viewing the surgical field through the microscope 100. The computing device 118 can generate a less smooth transition between glare spots and non-glare spots by selecting a lower blurring parameter. A less smooth transition can be useful for an observer 102 that prefers only a limited area of the visual field to be dimmed (e.g., only those portions with a brightness value exceeding the threshold brightness parameter). For example, a user specified blurring parameter can be received at the user interface 120 (FIG. 2).

In some embodiments, the computing device 118 can output a visual representation of the light received at the image sensor/camera 124 to a display device 126. For example, processing the received light to generate image data (step 14) can include any one or more signal processing steps to prepare the image data for display via the display device 126, including noise reduction, filtering, sharpening, contrast manipulation, etc. The display device 126 can be in communication with the computing device 118. In some embodiments, the display device 126 is part of the microscope 100. For example, the display device 126 can be a monitor disposed on or coupled to the microscope 100 to allow viewing by the observer 102 and/or other observers. In some embodiments, the display device 126 can be a separate component that is not part of the microscope 100 itself, and rather is in communication with the computing device 118 and the microscope 100. In various embodiments, the display device 126 can be a liquid crystal display (LCD), a light emitting diode liquid crystal display (LED-LCD), a digital micromirror device (DMD), heads up display, near to eye display, and/or other suitable display device. For example, the display device 126 can include transmissive elements (e.g., a backlit LED-LCD) or front-illuminated reflective elements.

In some embodiments, the visual representation output to the display device 126 can include the glare identified at 16. For example, an observer 102 and/or other observers viewing the surgical procedure via the display device 126 can see glare or high brightness light from the surgical field. At the same time, the optical element 114 can limit the glare or high brightness light for an observer 102 viewing the surgical procedure via the microscope optics. In some embodiments, the method 10 can include modifying the portions of the image data associated with the glare to limit the glare in the visual representation of the image data. The computing device 118 can output the visual representation of the modified image data to the display device 126. For example, glare or high brightness light can be limited for the observer 102 and/or others viewing the surgical procedure both via the display device 126 (with processed image data) and through the microscope optics (with the optical element 114).

As described herein, user-specified values for the threshold brightness parameter, the blurring parameter, and the dimming parameter can be received at the user interface 120. The functionality provided by the optical element 114 can be selectively turned on or off with the user specified values. For example, the threshold brightness parameter can be selected such that no light reflected from the surgical field is identified as glare. As a result, no light will be blocked by the optical element 114. In some embodiments, the dimming parameter can be chosen such that no light is blocked, even when identified as glare.

The microscope 100 discussed herein can be a monocular or binocular microscope. It is understood that the microscope 100 can include one eyepiece for each eye of one or more observers 102 (e.g., two eyepieces each for a surgeon and an assistant). The teaching of the present disclosure can be implemented such that light associated with glare is reduced in one or more eyepieces. The microscope 100 can be a compound, stereo, or digital microscope. The teaching of the present disclosure can be implemented in one or more optical paths of the microscope 100. For example, one optical element 114 can be implemented in the single optical pathway between the observer 102 and the surgical field in a compound or digital microscope. For example, one optical element 114 can be implemented in each of the two optical paths between the observer 102 and surgical field in a stereo microscope. In some embodiments, glare is blocked by the optical element 114 before being split to each optical pathway associated with the eyes of a single observer 102 and/or multiple observers 102. While FIG. 2a illustrates that various components (e.g., the user interface 120, the display device 126, the computing device 118, the voltage source 116, the image sensor/camera 124) are separate from the microscope 100, it is understood that in some embodiments, one or more of those components can be integrated in the microscope 100. For example, the computing device 118, the voltage source 116, and the image sensor/camera 124 can be integrated in the microscope 100.

Figure 2B:
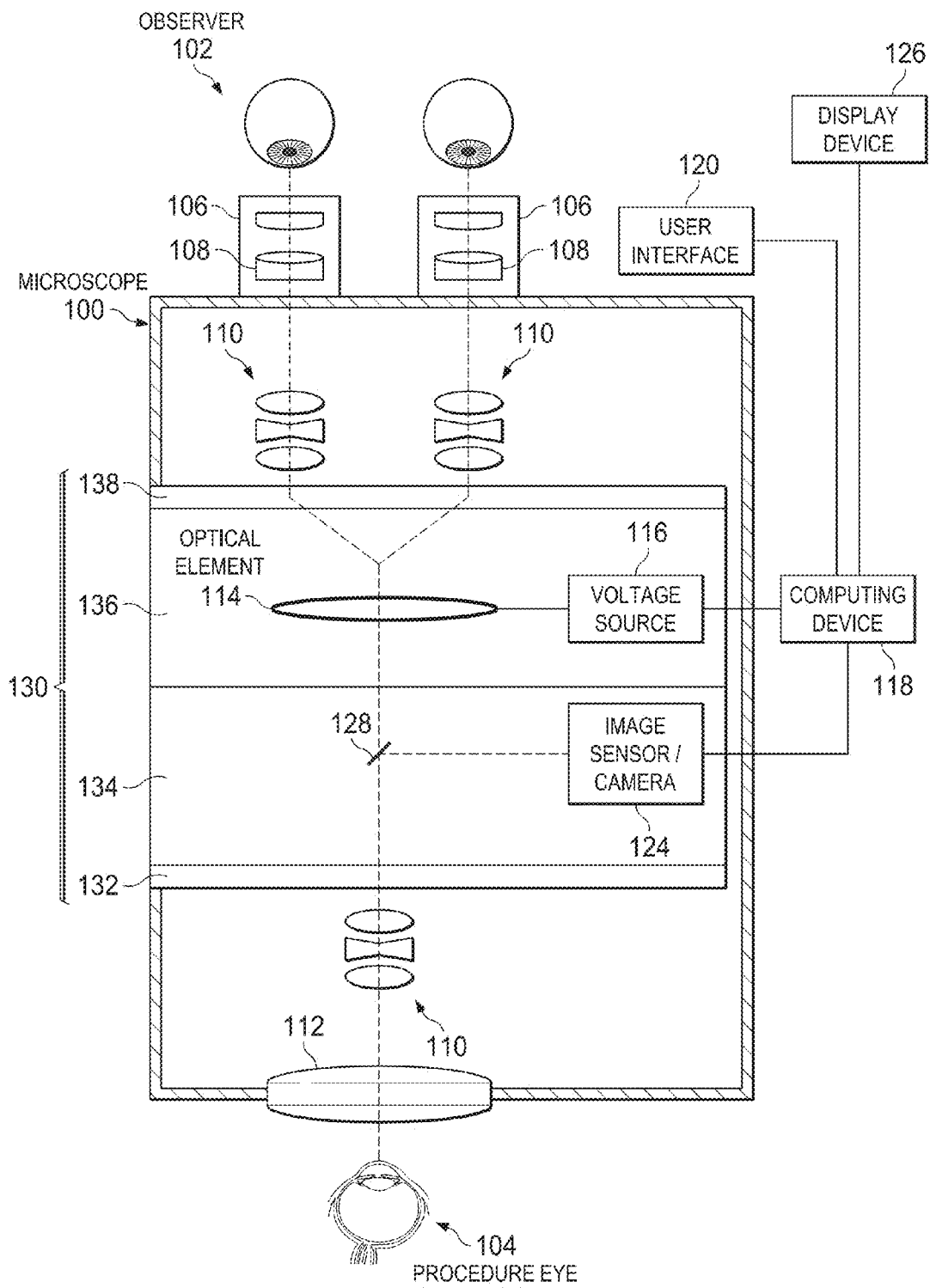
FIG. 2b is a diagram illustrating an exemplary ophthalmic surgical microscope according to an aspect of this disclosure.

FIG. 2b illustrates an exemplary ophthalmic surgical microscope 100. The microscope 100 of FIG. 2b is substantially similar to the microscope 100 of FIG. 2a, including the optical element 114, the voltage source 116, and the image sensor/camera 124, among other components. In the embodiment illustrated in FIG. 2b, the microscope 100 includes an array 130 of modules having components that are capable of acting on the light reflected from the procedure eye 104. For example, one of the modules 132, 134, 136, 138 can include an optical filter for removing certain wavelengths of light (e.g., laser light used during the surgical procedure) that could be harmful for the observer 102.

The modules 132, 134, 136, 138 are configured to be removably coupled to the microscope 100. That is, a user (e.g., the observer 102, a surgeon, another physician, nurse, technician, etc.) can selectively add or remove one or more of the modules 132, 134, 136, 138 to facilitate viewing through the microscope 100, e.g., based on the preferences of the observer 102. Because the modules 132, 134, 136, 138 are configured to be removably coupled to the microscope 100, the image sensor/camera 124 and/or the optical element 114 can be selectively included in the microscope 100, based on, e.g., the preferences of the observer 102. In that regard, the modules 132, 134, 136, 138 are sized and shaped to be removably, mechanically coupled to the microscope 100. The modules 132, 134, 136, 138 also facilitate optical coupling with another of the modules 132, 134, 136, 138 and/or other components of the microscope 100 (e.g., the objective lens 112 and/or the optical components 106, 108, 110). Accordingly, light reflected from the procedure eye 104 can travel through the modules 132, 134, 136, 138 to the observer 102. The modules 132, 134, 136, 138 are also configured to facilitate electrical coupling with another of the modules 132, 134, 136, 138 and/or other components of the microscope 100 (e.g., the computing device 118, the user interface 120, and/or the display device 126). While four modules 132, 134, 136, 138 are illustrated in FIG. 2b, it is understood that different embodiments can include more or fewer modules. For example, the array 130 of FIG. 2c includes three modules 132, 138, and 140.

Figure 2C:
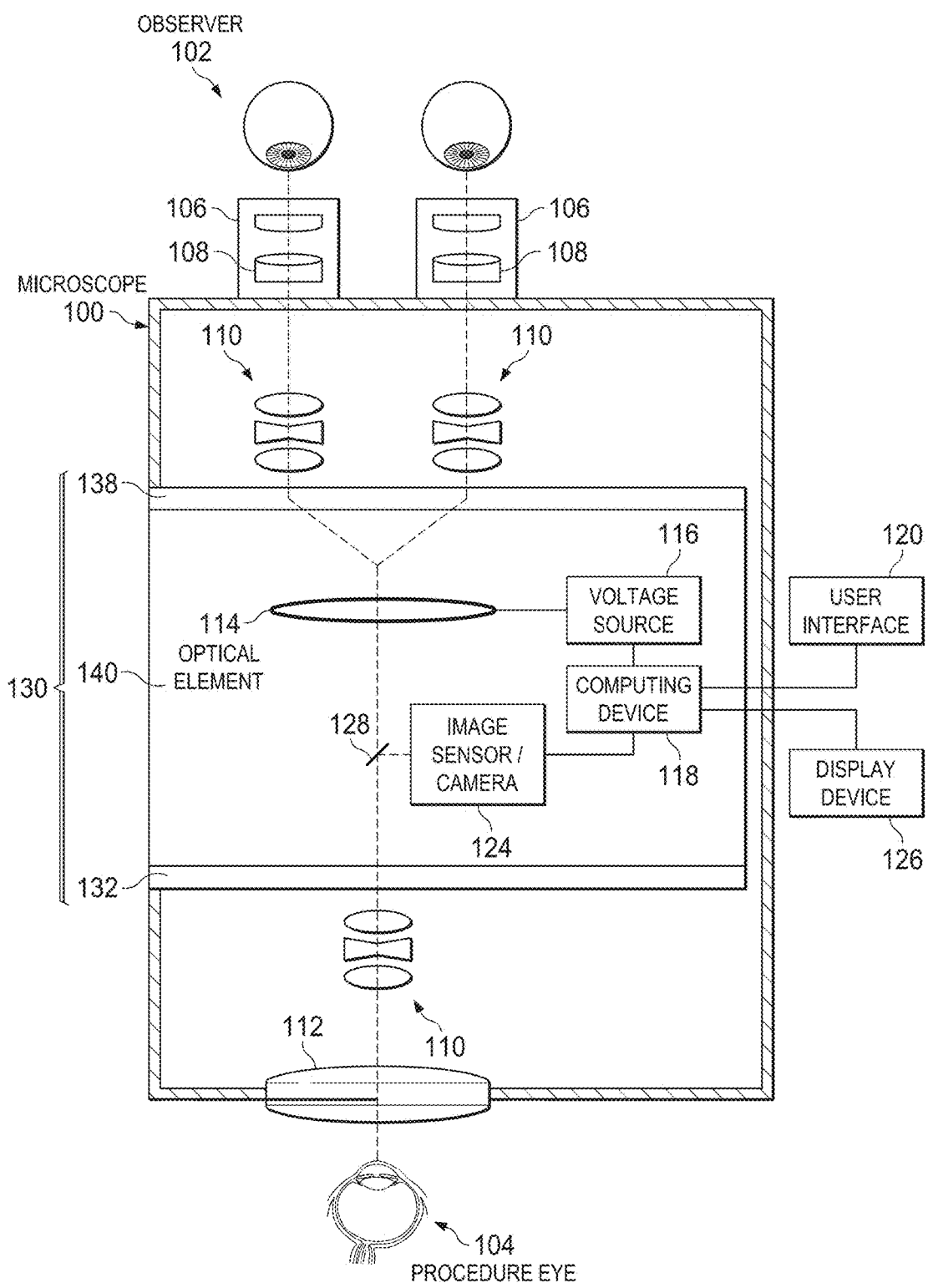
FIG. 2c is a diagram illustrating an exemplary ophthalmic surgical microscope according to an aspect of this disclosure.

The modules 132, 134, 136, 138 are capable of acting on the light reflected from the procedure eye 104. In that regard, one or more optical, opto-electronic, and/or electronic components can be disposed in the modules 132, 134, 136, 138. For example, the module 134 includes the image sensor/camera 124. The module 134 can also include the beamsplitter 128 to direct light reflected from the procedure eye 104 to the image sensor/camera 124. For example, the module 136 includes the optical element 114. The module 136 can also include the voltage source 116 that is in communication with the optical element 114. In the embodiment of FIG. 2c, the computing device 118 is a separate component that is not part of the microscope 100 itself. The modules 134 and 136 are coupled to the microscope 100 such that the optical element 114, the voltage source 116, and/or the image sensor/camera 124 are in communication with the computing device 118. The microscope 100 and/or the modules 132, 134, 136, 138 can include other components (e.g., wires, contacts, interfaces, etc.) for facilitating electrical, optical, and/or data communication between the optical element 114, the voltage source 116, the computing device 118, the image sensor/camera 124, etc. In some embodiments, the modules 132 and 138 include various other components to facilitate the view of the observer 102 of the procedure eye 104. In some embodiments, the modules 132 and 138 are placeholders that permit light to pass through, such as when the observer 102 does not require additional components to act on the light reflected from the procedure eye 104.

In various embodiments, different combinations of components can be included in a given module. For example, in the embodiment of FIG. 2b, the optical element 114 and the image sensor/camera 124 are disposed in different modules. In some embodiments, the optical element 114 and the image sensor/camera 124 are disposed in the same module. In the embodiment of FIG. 2c, the module 140 can include the optical element 114, the image sensor/camera 124, and the computing device 118. The microscope 100 of FIG. 2c is otherwise substantially similar to the microscope 100 of FIGS. 2a and 2b. Thus, the optical element 114 and the features described herein for glare reduction can be implemented in the microscope 100 by acquiring only a module (e.g., the module 136, the module 140, etc.). That is, a hospital or other ophthalmic services provider can advantageously avoid the acquisition of entire surgical microscope that includes the optical element 114, which can be a large capital expenditure. In the embodiments of the FIGS. 2b and 2c, it is understood that the optical element 114, the voltage source 116, the image sensor/camera 124, the computing device 118, the user interface 120, and/or the display device 126 can be in communication via one or more of the modules (e.g., modules 134, 136, 140), without interaction with the microscope 100. For example, the user interface 120 and the display device 126 can be directly communicatively coupled with the computing device 118.

Embodiments as described herein can provide devices, systems, and methods that provide a reduced glare ophthalmic surgical microscope including an optical element controllable to selectively limit the transmission of light associated with glare from the surgical field. The examples provided above are exemplary only and are not intended to be limiting. One skilled in the art may readily devise other systems consistent with the disclosed embodiments which are intended to be within the scope of this disclosure. As such, the application is limited only by the following claims.

The invention claimed is:

1. A method of operating a surgical microscope positioned in an optical pathway between a surgical field and an observer, the method comprising:
   receiving light reflected from the surgical field at an image sensor of the surgical microscope;
   processing the received light to generate image data;
   identifying portions of the image data representative of glare from the surgical field; and
   controlling an optical element positioned in the optical pathway to limit transmission of light associated with the glare.

2. The method of claim 1, further comprising:
   identifying portions of the optical element through which the light associated with the glare will be transmitted to the observer that correspond with the identified portions of the image data.

3. The method of claim 2, wherein controlling the optical element includes:
   generating a control signal that selectively controls the identified portions of the optical element to limit the transmission of the light associated with the glare.

4. The method of claim 3, wherein controlling the optical element includes:
   controlling portions of the optical element other than the identified portions to transmit the light reflected from the surgical field to the observer.

5. The method of claim 1, wherein the optical element comprises:
   a liquid crystal array.

6. The method of claim 5, wherein controlling the optical element includes:
   providing the control signal to a voltage source in communication with the liquid crystal array.

7. The method of claim 6, further comprising:
providing a voltage to the liquid crystal array based on the control signal such that pixels of the liquid crystal array through which the light associated with the glare will be transmitted to the observer are modified to limit the transmission of the light.

8. The method claim 1, wherein controlling the optical element includes limiting the transmission of light associated with the glare while not limiting the transmission of light that is not associated with the glare.

9. The method of claim 1, wherein controlling the optical element includes limiting the transmission of light associated with the glare in a manner different than the transmission of light not associated with the glare.

10. A surgical microscope positioned in an optical pathway between an observer and a surgical field, the microscope comprising:
an image sensor configured to receive light reflected from the surgical field;
a computing device in communication with the image sensor, the computing device configured to:
identify portions of the light received at the image sensor associated with glare from the surgical field; and
generate a control signal to limit the transmission of the light associated with the glare to the observer; and
an optical element in communication with the computing device and configured to selectively limit the transmission of the light associated with the glare to the observer in response to the control signal.

11. The surgical microscope of claim 10, wherein the computing device is further configured to:
identify, based on the identified portions of the light received at the image sensor, corresponding portions of the optical element through which the light associated with the glare will be transmitted to the observer.

12. The surgical microscope of claim 11, wherein:
the optical element is controllable to selectively limit the transmission of the light associated with the glare through the identified portions of the optical element.

13. The surgical microscope of claim 10, wherein the optical element comprises:
a liquid crystal array.

14. The surgical microscope of claim 13, further comprising:
a voltage source in communication with the optical element, the computing device configured to provide the control signal to the voltage source.

15. The surgical microscope of claim 14, wherein the voltage source is configured to:
provide a voltage to the liquid crystal array based on the control signal such that pixels of the liquid crystal array through which the light associated with the glare will be transmitted to the observer are modified to limit the transmission of the light.

16. The surgical microscope of claim 14, wherein the optical element and the voltage source are disposed in a removable module.

17. The surgical microscope of claim 14, wherein the optical element, the voltage source, and the image sensor are disposed in a removable module.

18. The surgical microscope of claim 14, wherein the optical element, the voltage source, the image sensor, and the computing device are disposed in a removable module.

19. The surgical microscope of claim 10, wherein the optical element is disposed in a removable module.

20. A surgical microscope positioned in an optical pathway between an observer and a surgical field, the microscope comprising:
an image sensor configured to receive light reflected from the surgical field;
a computing device in communication with the image sensor, the computing device configured to:
identify portions of the light received at the image sensor having a brightness value exceeding a threshold brightness parameter; and
generate a control signal to limit the transmission of the light having a brightness value exceeding a threshold brightness parameter; and
an optical element in communication with the computing device and configured to selectively limit the transmission of the light having the brightness value exceeding the threshold brightness parameter, wherein the computing device is further configured to identify portions of the optical element through which the light having the brightness value exceeding the threshold brightness parameter will be transmitted and to generate the control signal to selectively limit the transmission of the light through the identified portions of the optical element.

* * * * *